(12) United States Patent
Taylor et al.

(10) Patent No.: US 6,941,033 B2
(45) Date of Patent: Sep. 6, 2005

(54) METHOD AND DEVICE FOR MANIPULATING MICROSCOPIC QUANTITIES OF MATERIAL

(75) Inventors: Rod Taylor, Gloucester (CA); Cyril Hnatovsky, Ottawa (CA)

(73) Assignee: National Research Council of Canada, Ottawa (CA)

( * ) Notice: Subject to any disclaimer, the term of this patent is extended or adjusted under 35 U.S.C. 154(b) by 81 days.

(21) Appl. No.: 10/602,604

(22) Filed: Jun. 25, 2003

(65) Prior Publication Data

US 2004/0051037 A1 Mar. 18, 2004

Related U.S. Application Data

(60) Provisional application No. 60/391,412, filed on Jun. 26, 2002, and provisional application No. 60/391,087, filed on Jun. 25, 2002.

(51) Int. Cl.[7] ................................................. G02B 6/00
(52) U.S. Cl. ............................ 385/12; 385/117; 605/15
(58) Field of Search ............................. 385/12, 117, 118; 250/234, 288; 606/15; 607/89

(56) References Cited

FOREIGN PATENT DOCUMENTS

WO    WO 02/16070 A2    2/2002

OTHER PUBLICATIONS

Stockle, Raoul et al., "High-quality near-field optical probes by tube etching", Applied Physics Letters, vol. 75, No. 2, Jul. 1999, pp. 160–162.
Binnig, G. et al., "Atomic force microscope", Physical Review Letters, vol. 56, No. 9, Mar. 1986, pp. 930–933.
Luo, Zong–Ping et al., "An optical spin micromotor", Applied Physics Letters, vol. 76, No. 13, Mar. 2000, pp. 1779–1781.
Cullum, Brian M. et al., "The development of optical nanosensors for biological measuements", TIBTECH, vol. 18, Sep. 2000, pp. 388–393.
Novotny, Lukas et al., "Theory of nanometric optical tweezers", The Americal Physical Society, vol. 79, No. 4, Jul. 1997, pp. 645–648.
Tan, Weihong et al., "Development of submicron chemical fiber optic sensors", American Chemical Society, Dec. 1992, vol. 64, No. 23, pp. 2985–2990.
Taylor, R.S. et al., "Combined AFM–NSOM scanning probe microscopy for photonic applications", Microscopy and Analysis, May 1999, pp. 15–17.
Subramanian, Vinod, "Biological applications of multiphoton NSOM with multiple spectroscopic modes", The Americas Microscopy and Analysis, Jan. 2001, pp. 9–11.
O'Neil, A.T. et al., "Manipulation of metallic particles in inverted optical tweezers", Conference on Lasers and Electro–optics, 1999, pp. 428–429.
Valaskovic, Gary A., et al, "Attomole–sensitivity electrospray source for large–molecule mass spectrometry", Anal. Chem., 1995, vol. 67, No. 20, Oct. 1995, pp. 3802–3805.

*Primary Examiner*—Phan T. H. Palmer
(74) *Attorney, Agent, or Firm*—Marks & Clerk; Richard J. Mitchell

(57) ABSTRACT

A method of manipulating a microscopic quantity of material is disclosed wherein an optical fiber probe having a sharp tip with a hole fabricated therein is used to extract the material. The hole is sufficiently small that upon immersion of the sharp tip in the material a virtual seal forms to inhibit penetration of the material into the hole. A laser pulse is sent down the fiber probe to disrupt the seal and promote entry of the material into the hole. The probe can also be used in a reverse manner to deliver trapped material from the hole into a targeted region. The bole also permits an annular light intensity distribution at and near the exit of the probe tip which can be used to optically trap particles.

28 Claims, 6 Drawing Sheets

METHOD AND DEVICE FOR MANIPULATING MICROSCOPIC QUANTITIES OF MATERIAL

CROSS-REFERENCE TO RELATED APPLICATIONS

This application claims the benefit under 35 USC 119(e) of U.S. provisional application Ser. No. 60/391,087 filed on Jun. 25, 2002, and U.S. provisional application Ser. No. 60/391,412 filed on Jun. 26, 2002.

FIELD OF THE INVENTION

This invention relates to the field of material handling, and in particular to a method and a probe for handling extremely small quantities of material, for example, in the order of attoliters (1 attoliter=$10^{-18}$ liter) to zeptoliters (1 zeptoliter=$10^{-21}$ liter). The invention is applicable to the performance of ultrasmall volume biopsies, single-molecule fluorescence sampling, injection of ultrasmall quantities of biological material, and the nanomanipulation of particles and biological material.

BACKGROUND OF THE INVENTION

In a number of fields, particularly the medical field, there is an emerging need to sample and manipulate extremely small volumes of material. These volumes may be in the order of one attoliter, where 1 attoliter=$10^{-18}$ liter to a number of zeptoliters (1 zeptoliter=$10^{-21}$ liters). For example, one may need to remove an ultrasmall volume of material from a specific location inside a biological sample such as a cell in order to perform an analysis of the constituents, for example, using a mass spectrometer. There is also need to perform an optical analysis (e.g. fluorescence) on the collected volume of material. In some cases the sampled volume can be so small (10–100 zeptoliters) that it contains on average a single analyte molecule at any given time even for high solution molar concentrations (200 $\mu$M). There may also be a need to inject small quantities of trapped material into a cell. Finally there is a need to optically trap particles such as a microscopic bead containing a drug or sensor and move it to a desired location.

Currently, small amounts of material can be picked up on the surface of sharp tipped probes. Such probes can include atomic force microscopy (AFM) probes and Near-Field Scanning Optical Microscopy (NSOM) probes. The most effective probes are those which use special coatings to enhance adherence and selectivity. Selectivity is critical to ensure that only targeted material is picked up. However these coatings add a good deal to the complexity of the procedure and also have restricted application. Tapered micropipettes can be used to extract small volumes (picoliter to femtoliter i.e., $10^{-12}$ to $10^{-15}$ liters, respectively) of material. However, it is believed that there is currently no method of extracting attoliter or smaller volumes of targeted biological material into a precision reservoir without using special coatings to enhance adherence and selectivity.

It is also difficult for micropipette probes to control the volume of extracted material. Tapered micropipette probes or pulled capillary tubing probes can be constructed to have small apertures (100 nm) and are hollow inside to accept the uptake of material. Due to the hollow nature of these probes, i.e., unrestricted and unconfined in one direction, it is difficult to extract a predetermined volume from a sample and to keep that volume intact at the end of the probe tip. These types of probes have not been successfully used to extract attoliters of material from within a biological sample. Suction techniques designed to extract material become very difficult to operate for sub-micron sized channels.

Light can be delivered down a micropipette to perform an optical analysis of biological material trapped inside the probe tip. The extracted material can also be optically probed externally using confocal or standard fluorescence microscopy techniques with lateral resolutions of $\leq \lambda/2$. However, tapered micropipettes are very inefficient at delivering light to the tip region due to their poor light guiding properties. Any fluorescence signal which returns back through such a probe would be extremely weak. It is possible to collect the fluorescence signal from the trapped material externally using confocal and other microscopies. However they require a separate and often quite sophisticated optical set-up. In addition the optical measurement can only be performed with the probe tip at or near the focus of a microscope objective and are limited to spectroscopic sampling volumes of femtoliters or larger due to the diffraction limit of light.

In another application, very small but known volumes (e.g., attoliters) of trapped material contained in a probe e.g., DNA, or a microsphere containing a drug or a sensor must be transferred to a desired location inside another material, such as the nucleus of a cell without damaging the cell. A similar problem is how to inject a small controlled volume of extracted material into a mass spectrometer for analysis. Tapered micropipettes are currently used to deliver small volumes of biological material into a cell. Tapered capillary tubes and tapered micropipettes together with electrospray techniques, for example, can be used to eject material into a mass spectrometer. Laser radiation sent down a tapered micropipette can be used to ablate material collected at the end of the tip to inject it onto a surface. However, the volume of material ejected from micropipette probes is typically in the picoliter to femtoliter range. Tapered micropipettes or capillary tubes have not been used to inject attoliter or smaller volumes of material into a cell or into a mass spectrometer.

Another problem is the trapping and manipulation, on a nanoscale of tiny particles, droplets of liquid or biological material such as cells and their transfer to a desired location. Focused light beams have been used to form optical tweezers to trap, move and release small particles as well as biological material. Optical tweezers based upon focused beams of light require precision alignment and are restricted to certain fields of use which permit access of the highly focused light beams to the particles e.g. non-turbid media, thickness of media must be less than the working distance of the lens, need for spherical aberration corrected lenses etc.

SUMMARY OF THE INVENTION

In accordance with the invention laser radiation is used to initiate uptake of material, such as biological material, into a small hole fabricated into the tip of a tapered optical fiber probe. The hole has a sufficiently small diameter (e.g. 100 nm) and depth (hundreds of nm) such that biological material or fluids have great difficulty penetrating deeply into the high aspect ratio (defined as the ratio of depth:diameter) hole because of surface tension and the need to displace the fluid (e.g. air) inside the hole. These effects create a virtual "seal" at the material/hole interface. This applies to the case where there has been no special wetting or preparation of the hole to more easily permit entry of material into the hole. The size of the hole required to create a seal will depend on the viscosity of the fluid i.e. the more viscous the fluid the larger the hole size can be.

It is preferable to create the hole in a sharp-tipped probe (tip diameter <1 μm) to enable the probe tip to penetrate into e.g., a cell without damaging it. One or more laser pulses sent down the fiber probe can be used to disrupt the virtual "seal" at the hole/material interface allowing air, for example, to leave the small volume of the probe and biological material to enter. The technique also applies to the case where the hole may be filled with low viscosity fluid (i.e. water-like) which is then ejected to draw in a high viscosity fluid (e.g. containing DNA).

Accordingly therefore in one aspect the invention provides a method of manipulating a microscopic quantity of material, comprising providing an optical fiber probe having a tip with a hole fabricated therein, said hole being sufficiently small and sufficiently deep that upon immersion of said sharp tip in said material a virtual seal forms to inhibit penetration of said material into said hole; immersing said tip in said material; and sending laser pulse radiation through said optical fiber probe to disrupt said virtual seal and thereby promote entry of said material into said hole.

This concept can also be applied to arrays of tiny holes with adjoining optical waveguides on a biochip. These holes can be made in accordance with the technique described in our U.S. patent application Ser. No. 10/431,442, filed May 8, 2003 and entitled "Method of Fabricating Sub-Micron Structures in Transparent Dielectric Materials", the contents of which are herein incorporated by reference.

In order to ensure that the targeted extracted sample is contained only in the small hole it is necessary to remove any material which might have accumulated on the outside surface of the probe without losing any material trapped in the hole. This can be done relatively easily using the small hole employed in the invention since just as it is difficult to put sample material into the small diameter, deep hole, it is also difficult to remove the material trapped within the hole compared to removing material from the exposed outer surfaces.

The very small probe volumes (attoliters to zeptoliters), especially those formed from high aspect ratio holes, can also be used directly to inhibit the escape of a trapped sample as it is directed through biological material, such as a cell, to a desired location, such as the nucleus, for injection.

The use of selective chemical etching of special single-mode fibers with appropriate core/cladding index of refraction profiles currently enables reproducible "attoliter to femtoliter" volume holes to be produced inside tapered conical structures which can efficiently deliver light to surround the hole. In future it may be possible to fabricate narrower hole diameter, deeper holes with selective chemical etching using made-to-order designer fibers. Smaller holes with volumes of zeptoliter to attoliter size can be fabricated using focussed-ion beam (FIB) technology.

In this specification, reference will be made to laser radiation and light transmission. It will be understood by persons skilled in the art that such terms are not limited to visible light, and include non-visible wavelengths, such as near-infrared.

In another aspect the invention provides a probe for manipulating small quantities of material, comprising an optical fiber having a tip with a hole fabricated therein, said hole being sufficiently small that upon immersion of said tip in said material a virtual seal forms to inhibit penetration of said material into said hole; and said optical fiber probe providing a waveguide to direct laser radiation to said hole to disrupt said virtual seal and thereby promote entry of said material into said hole.

In yet another aspect the invention provides a method of making a probe for manipulating small quantities of material, comprising forming a tip at the end of an optical fiber providing a waveguide to direct a laser pulse thereto; and forming a hole in said tip, said hole being sufficiently small that upon immersion of said tip in said material a virtual seal forms to inhibit penetration of said material into said hole.

In a still further aspect the invention provides a method of inserting a small quantity of material into a cell, comprising immersing in said material an optical fiber probe having a tip with a hole fabricated therein, said hole being sufficiently small that upon immersion of said tip in said material a virtual seal forms to inhibit penetration of said material into said hole; sending laser pulse radiation through said optical fiber probe to disrupt said virtual seal ejecting the material.

In another aspect invention takes advantage of the fact that the hole modifies the tapered silica waveguide (i.e. creates an interior air cladding) to form an annular light distribution at and near the exit surface of the fiber probe. In another version the fiber probe can be metalized. Removal of the metal from the top surface of the probe but not in the hole creates an annular-shaped light distribution at the exit surface. The annular light distribution can be used to trap particles externally close to but not at the probe tip. The metalized surfaces absorb laser radiation and can be used to rapidly heat or provide an acoustic impulse to the hole region to either extract or inject material.

BRIEF DESCRIPTION OF THE DRAWINGS

The invention will now be described in more detail, by way of example only, with reference to the accompanying drawings, in which:—

DETAILED DESCRIPTION OF THE PREFERRED EMBODIMENTS

As noted above, when a very small hole, typically having a diameter of ≈100 nm and a depth of at least 200 nm is immersed in a fluid, surface tension effects and the air within the hole act to prevent entry of the fluid into the hole. In effect they act to form a "virtual seal" closing off the hole. In accordance with the principles of the invention, such holes are formed in the tip of a probe, and laser radiation is employed to initiate uptake of biological material into the hole. The laser radiation is preferably in the form of a laser pulse or pulses sent down the fiber probe. The laser pulses disrupt the "seal" at the hole/material interface allowing air to leave the small volume of the probe and biological or other material to enter. It has not been previously thought possible to employ such very small holes for transferring fluids without using some wetting agent or preparing the holes in a separate process for fluid uptake.

This principle applies to other geometries such as arrays of holes with adjoining optical waveguides created in biochips. Our patent application Ser. No. 10/431,442 referred to above describes how to make such sub-micron diameter holes in dielectrics with adjoining waveguides. The controlled firing of laser pulses down various waveguides would permit the sampling on command of very small volumes (attoliters) of biological material, which could be moving over the top surface of arrays of holes. The sampling could be done as a function of time and at different locations on the biochip. The reverse process can also be used to eject material trapped in arrays of sub-micron holes.

Optical analysis of the biological material trapped inside a hole can be performed with the probe removed from the sample but still submerged in a liquid layer or in a 100% humidity environment covering the sample to prevent evaporation of the sample. If the probe is removed from this environment then some method of preventing evaporation of the trapped sample may be required. One such means described by Erik Litborn in PCT published patent application no. WO 98/33052, the contents of which are incorporated herein by reference, is to encapsulate the probe tip with a volatile liquid which is immiscible with the sample but which eventually evaporates when the sample is ready for analysis.

Figure 1:
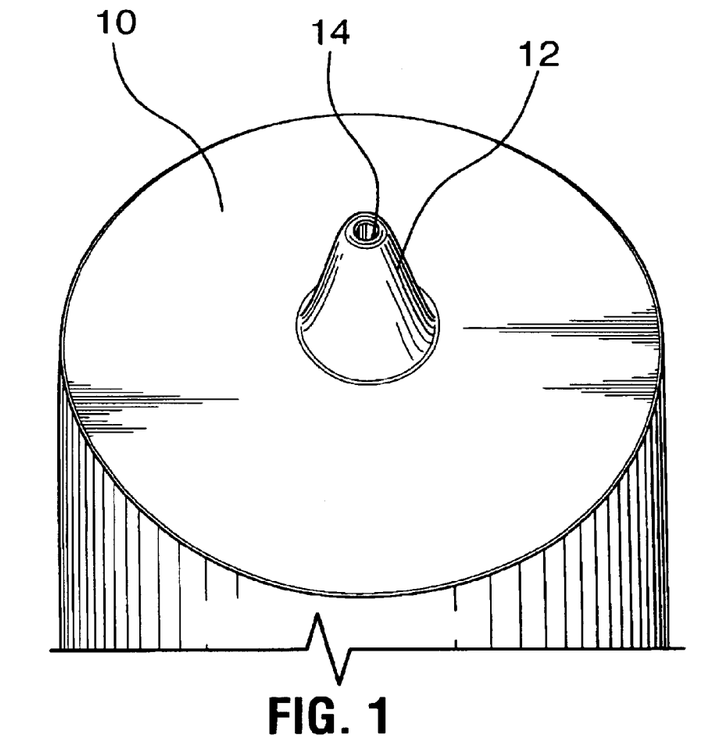
FIG. 1 shows two photographs of a chemically etched fiber nanoprobe, according to an embodiment of the invention.

Probes used in the invention can be made by several techniques. One technique starts with a commercially available high $GeO_2$ doped, single-mode, fused silica optical fiber used in telecom applications which when immersed in buffered oxide etchant, e.g., 6:1 BOE, i.e. 6 volumes of ammonium fluoride $NH_4F$ (40% by wt.) to 1 volume hydrofluoric acid HF (49% by wt.), preferentially etches the silica cladding with respect to the doped silica core to produce, as shown in FIG. 1, a conical structure 12 with a small diameter (e.g. a few hundred nm) hole 14 in it. The base of the conical structure 12 sits on top of the fiber core which is surrounded by the cladding 10.

Prior to selective chemical etching one can optionally etch the probe to reduce the fiber core plus cladding diameter (e.g. from 125 $\mu$m to 30 $\mu$m) over all or part of its length (this was done for the probe shown in FIG. 1 prior to etching the hole) to allow easier entry of the probe into sample material. This can be done without producing a significant hole or conical structure in the core region.

Figure 2A:
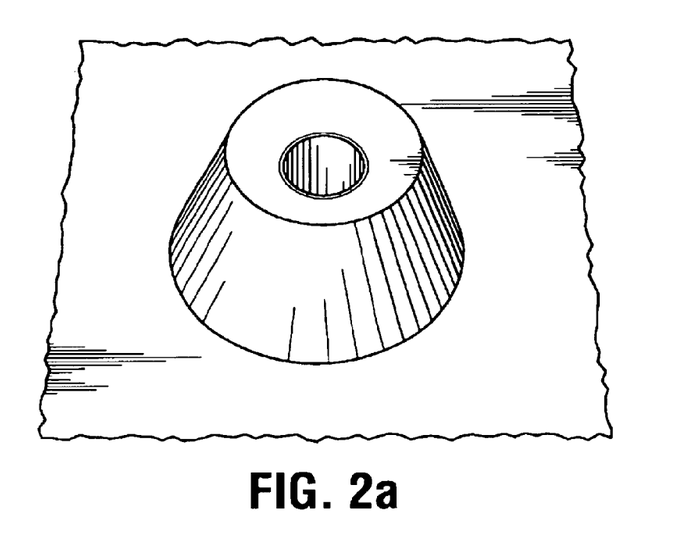
FIGS. 2a and 2b show two different selectively chemically etched hole volumes.
Figure 2B:
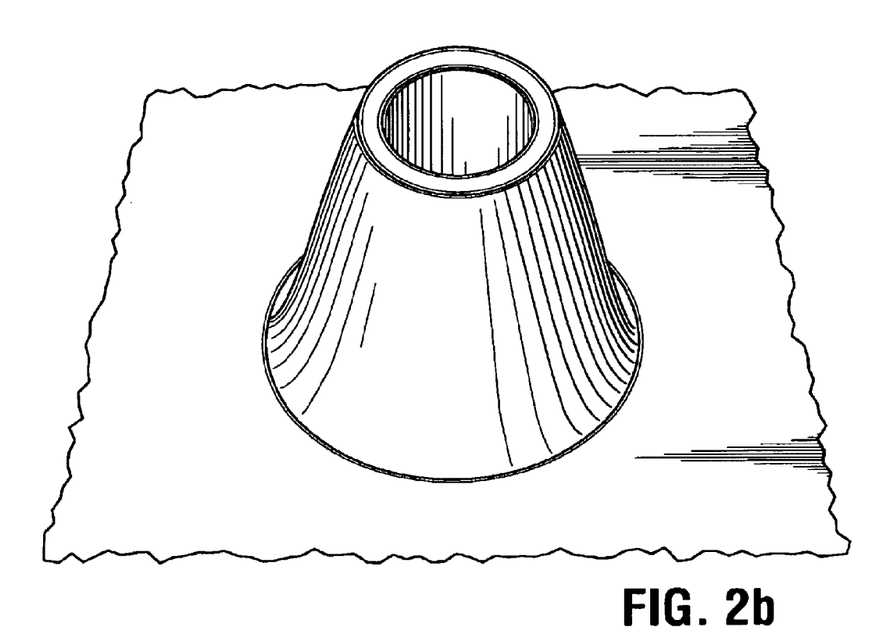

The hole diameter and depth can be controlled with the choice of etching parameters as well as with the choice of fiber to provide probes with different hole volumes. FIGS. 2a and 2b show close up scanning electron micrographs of two selectively etched holes having different volumes. These volumes can be made as small as tens of attoliters.

Figure 3:
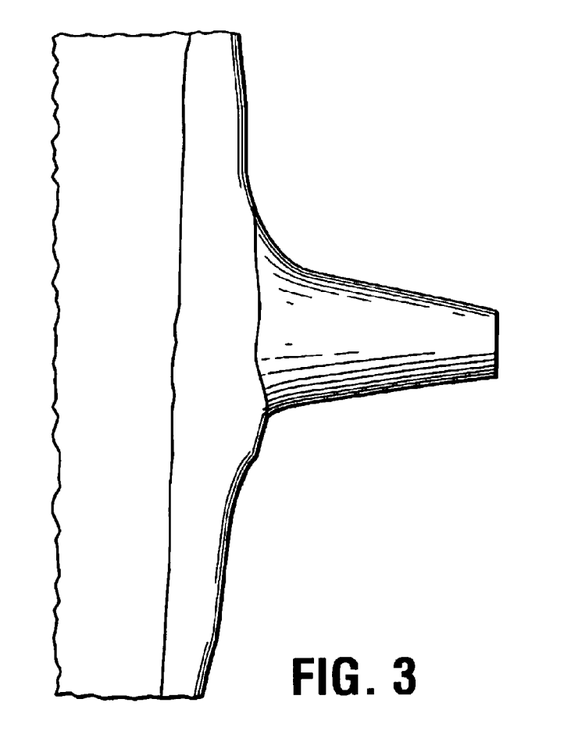
FIG. 3 is a photograph of a Focused Ion-Beam sectioned etched conical structure showing a 500 nm deep hole.

FIG. 3 shows a cross-section analysis obtained using a focused ion beam (FIB) to nanoslice a selectively etched conical structure fabricated as described above. This Figure shows that in this case a clean 500 nm deep hole was created inside the silica conical structure using selective chemical etching.

Figure 4A:
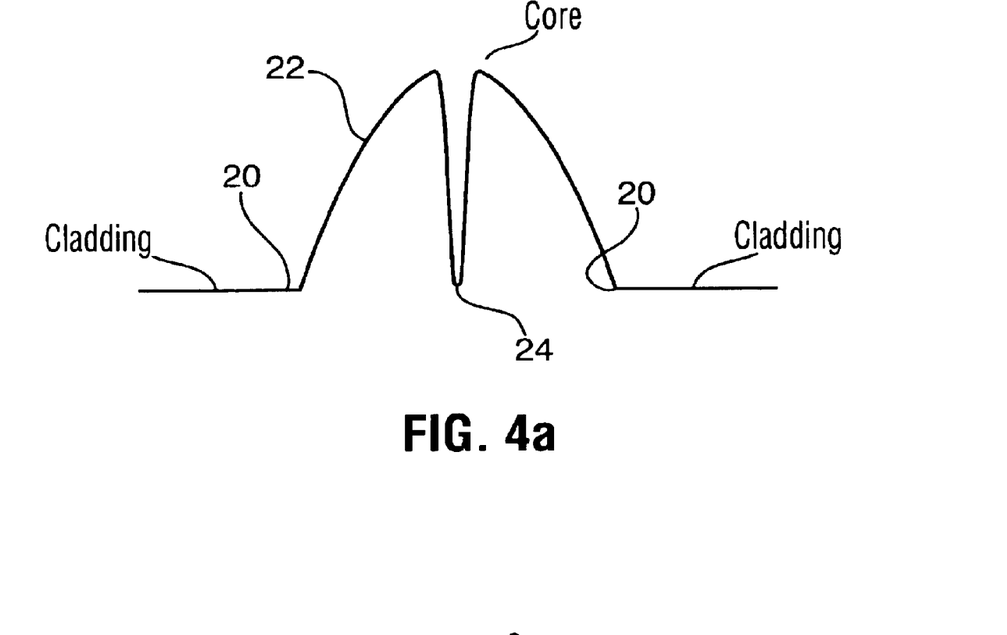
FIGS. 4a and 4b show preferred index of refraction profiles for selective chemical etching and FIB hole formation, respectively, which can be used in the fabrication of probes according to embodiments of the invention.

A preferred index of refraction profile across the circularly symmetric fiber core region which produces a tapered conical structure containing a narrow high aspect ratio hole is shown in FIG. 4(a). During the etching in BOE the low index (i.e. low dopant) regions of the fiber probe etch faster relative to the high index regions resulting in the transformation of the fiber core into a tapered conical structure with a hole in it. The index profile across the core should be approximately parabolic in shape 22 with a narrow (to enable fabrication of a small diameter hole) sharply defined low index center 24 which drops to an index level comparable to that of the cladding. The $GeO_2$ doping concentration should be high (e.g. relative core/clad index difference of 2%) to ensure strong differential etching of the cladding relative to the core to provide a steep, high conical structure. High ratios of $NH_4F$ to HF also assist in making a steeper conical structure.

This process can also be assisted by employing a $F_2$ doped cladding which etches faster than the undoped silica cladding. The fiber core diameter should preferably be large e.g., 8 $\mu$m so that after selective etching the conical structure is sufficiently high (e.g., 10 $\mu$m) to allow the conical structure to penetrate fully into a wide range of cells or other biological objects. At the same time there is a significant benefit to having a relatively short (10 $\mu$m) tapered region compared to slowly tapered pulled probes or tapered micropipettes (typical taper lengths of 100 $\mu$m–1 mm). The short taper length makes the probe tip stiffer which results in less flexing of the probe thereby making it easier to penetrate into a cell, for example. The width of the top portion of the conical structure should be small (say <1 $\mu$m) so that the tip readily penetrates into a cell and can be removed without producing any significant cell damage. At the same time if the tip diameter is too small then it becomes more difficult to deliver the required light intensity to effect the disruption of the seal. In order to achieve high light transmission to the apex of the tip the width of the annulus surrounding the hole should be near or larger than $\lambda/2n$, where n is the index of refraction of the propagating medium and $\lambda$ is the wavelength of light used. For silica glass n≈1.5 and for visible light, $\lambda/2n=200$ nm.

Since the construction of these probes requires only the appropriate choice of fiber and the use of selective chemical etching, which can be an automated batch process, arrays of these probes can be inexpensively constructed. It is also possible to bend these probes to form a cantilever so that they can be used with conventional atomic force microscopes in similar fashion to NSOM probes. This not only provides distance regulation for the probe tip but also a means of controlling the force that the probe tip exerts on a biological object.

Figure 4B:
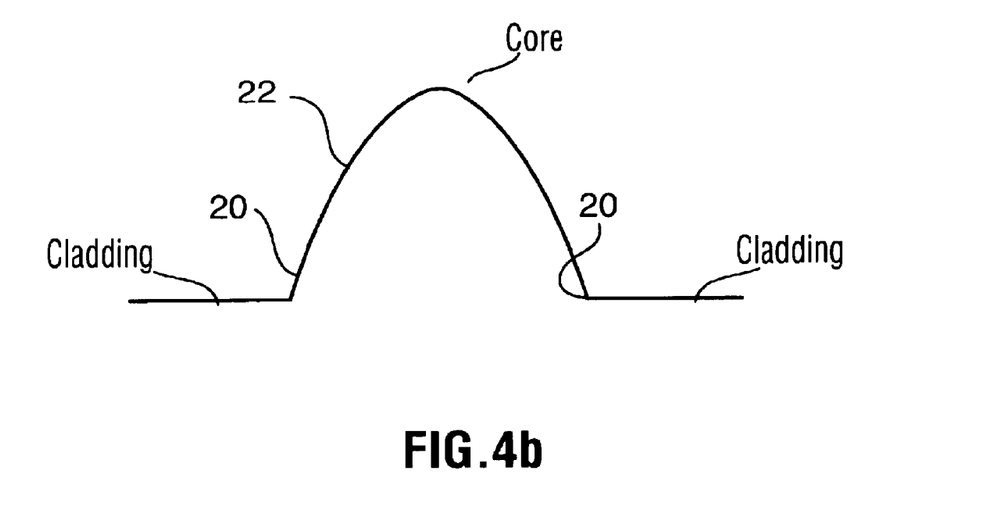
Figure 5:
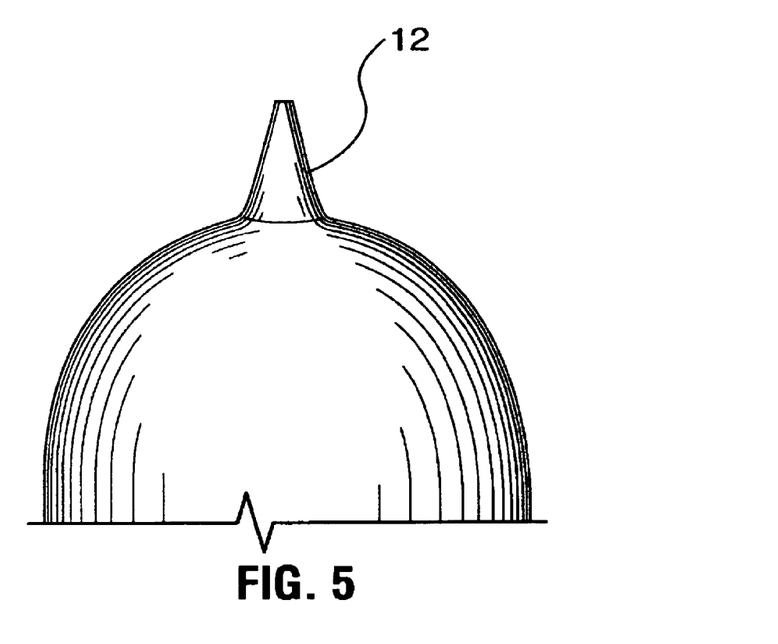
FIG. 5 shows a flat-topped conical structure on a hemispherically tipped fiber probe.

A second technique for fabricating the novel probes starts from optical fibers having the index of refraction profile similar to that shown in FIG. 4b. This is similar to the profile shown in FIG. 4a without the narrow center. It involves using a special, outside vapor deposition (OVD), high $GeO_2$ doped, 8 $\mu$m diameter, single-mode fiber, which is chemically etched (e.g. 6:1 BOE) to produce a tall flat-topped (i.e. no hole) conical structure 12 as shown in FIG. 5. The flat top is created by removing the fiber from the etchant before a sharp tip forms. Flat-topped diameters as small as 100 nm are possible.

Figure 6:
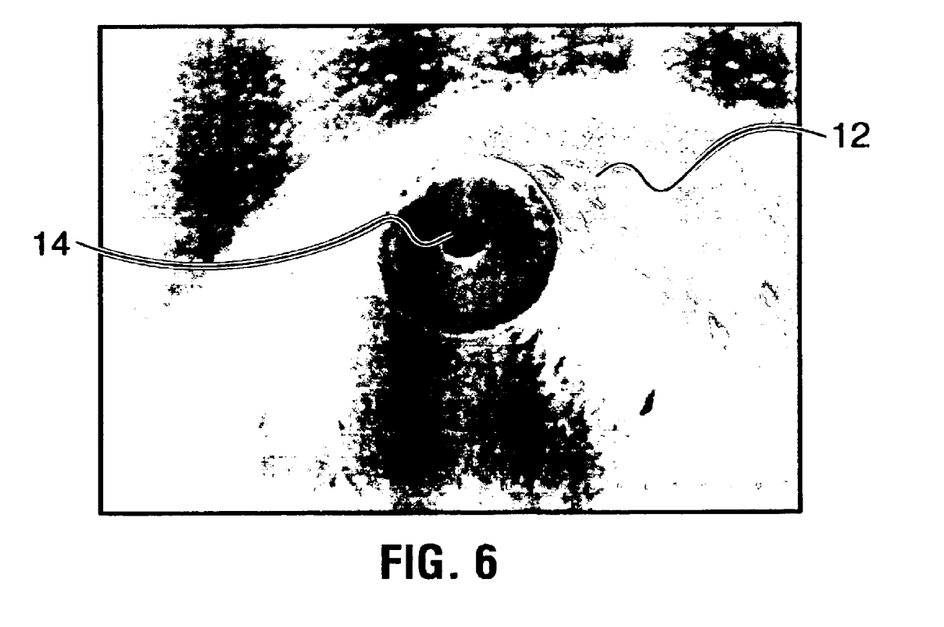
FIG. 6 shows an FIB hole drilled into a flat-topped conical structure.
Figure 7:
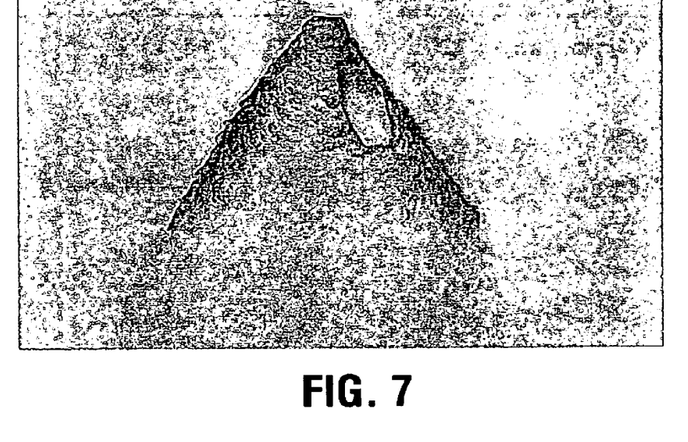
FIG. 7 shows an FIB hole drilled into a non-flat-topped metallized conical structure.

A focused ion beam (FIB) is used to drill a hole 14 of known depth (e.g., 600 nm) and diameter (e.g., 200 nm) into the 10 $\mu$m high conical structure as shown in FIG. 6. The probe can be coated with a thin metal coating to reduce charging effects during the FIB procedure. The coating can be removed after the hole has been drilled. Alternatively the hole can be drilled into a fully metalized (e.g. metal thickness of 100 nm) probe tip. The FIB process can be assisted by an etchant which selectively etches the FIB irradiated silica. In cases where it is desirable to make a small hole just in the metal coating e.g. for zeptoliter fluorescence sampling, it is advantageous to use a different etchant which assists the FIB process to remove the metal leaving the underlying silica untouched. The flat-topped structure shown in FIG. 6 enables the FIB operator to accurately target the focused ion beam to the center of the conical structure. It is important to form the flat-topped structure first. FIG. 7 demonstrates what typically happens when one tries to FIB a hole into a non-flattened tip of a metallized conical structure. Hole diameters both in a metal or in silica as small as 10 nm can be FIB drilled.

For FIB drilling a preferred index of refraction profile to produce a steep flat-topped conical structure is shown in FIG. 4(b). The large core diameter, highly doped single-mode fiber together with a high ratio of $NH_4F$ to HF produces a high conical structure which as discussed above is useful to allow only the conical structure to enter into a cell.

In order to further assist in ensuring a smooth entry of the fiber probe through biological material and into a cell a hemi-spherically shaped profile can be formed on the probe tip prior to the selective chemical etching as shown in FIG. 5. This can be accomplished by heating the probe end face in a spark discharge.

One could also use the FIB technique with pulled single-mode NSOM fiber probes in which the tapering is halted at diameters of 500 nm rather than the usual 50–100 nm tip sizes required for high resolution NSOM. One could use the FIB to slice the end off the probe to produce a flat-topped structure, or alternatively the metal on the tip can be removed by repetively pressing it on a flat smooth surface. The FIB can then be used to produce a narrow deep hole in the end face of the probe. It is also possible to use non-selective chemical etching to produce a pencil-like tapered fiber tip. If the chemical etching is stopped early before a sharp tip is formed then once again the FIB can be used to accurately drill a small hole in the tip region.

If the flat-topped probe is first entirely coated with metal and the FIB is used to remove an annular metal region from the top of the probe tip then the light escaping from the probe tip has an annular shaped intensity distribution. The benefit of an annular light distribution emerging from the probe tip is that it can be used to trap particles with a continuous wave laser as discussed in more detail below.

The light transmission through the selectively chemically etched conical tipped fiber probes described above is at least $10^3$ higher than through a tapered micropipette, which has very poor light guiding properties. The transmission properties of the probes described above are sufficiently high that light can be sent down the probe to produce a fluorescence signal from an ultra small volume (zeptoliter to attoliter) of material which can return through the same fiber to the probe entrance to be detected. The ability of the fiber probe to make fluorescence measurements on the extracted volume at different locations of the probe (e.g., inside a cell, just outside the cell, outside the biological sample etc.) and under different conditions (e.g. as the probe tip is heated or cooled or placed in a magnetic field etc.) provides greater flexibility and simplification to the optical set-up compared to confocal or other optical microscopies.

Since it is difficult to extract attoliters of material into a small reservoir inside a probe it follows that once the material is inside it cannot easily be removed. This allows the probe tip to be inserted into biological material and placed at the desired location without the "trapped material" e.g. a sub-micron sized bead containing a sensor or a drug, escaping or other material entering into the hole. In the case of a microbead, it is possible that the bead could be placed into the hole by mechanical means. Laser radiation can now be transmitted down the probe to rapidly heat the trapped material due to 1) direct absorption of the laser light by the trapped material (case for an non-metalized probe) causing rapid evaporation and or an acoustic impulse leading to ejection, 2) absorption of laser radiation by a metal coating near the hole but not in the hole rapidly transferring heat to the contents of the hole. 3) laser radiation heating of a metal coating covering only the hole itself (in this case a very small laser controlled nanoheater can be formed), and 4) absorption of the laser radiation by a thin layer of imbedded Ga ions (produced in the FIB drilling) to rapidly heat the sample (a second case for a non-metalized probe). These laser heating options can also be applied to the case of extracting a small volume of material using rapid heating leading to evaporation and/or acoustic disruption of the "seal".

The laser heating can also be used to launch a particle placed in the hole. The rapid heating of a volume of trapped fluid below the particle can cause an explosive ejection of the fluid and the particle. One can match the hole size and the object size to create an optimum volume of trapped liquid and optimum sealing of the hole to maximize the expulsion force to launch the object. The above effects can also be accomplished for an array of holes with adjoining waveguides on a glass chip as described in U.S. patent application Ser. No. 10/431,442 referred to above. In this case the metal can be removed from the surface by polishing the glass surface leaving the metal inside the holes.

A suitable laser source used to produce an acoustic "impulse" to dislodge the trapped material would be a Nd:YAG laser operating at $\lambda=1.06$ $\mu$m and with a pulse duration ranging from ns to $\mu$s and pulse energies in the range of nJ to $\mu$J. If the laser radiation is absorbed by a metal coating at the probe tip then the laser wavelength is not critical and any suitable pulsed ultra-violet to near-infrared laser can be used.

It has been suggested (see A. O'Neil and M. Padgett, Conference on Lasers and Electro-optics, Opt. Soc. of America, Washington, D.C., USA, pp. 428–429, 1999) that the preferred focussed cw laser intensity distribution to optically trap and manipulate micron sized metal and dielectric particles is an annular one. In the case of an non-metalized fiber probe the presence of a hole inside the conical structure creates an automatic annular intensity profile since the low index of refraction of air provides a cladding layer both inside and outside the annular silica rim structure to assist in guiding light. When the probe is immersed in liquids the strong guiding effect of an air cladding is lost due to the closer index of refraction of glass (1.5) and water (1.33). In this case it may be advantageous to totally coat the probe tip with metal and then use a FIB to nanoslice off the top metal layer to expose an annular silica light guiding region around a metalized hole. One could also use the FIB to remove an annular pattern of metal directly from the top surface of a fully metalized flat-topped conical tapered structure to produce an annular waveguiding region. Another means of creating an annular profile is by gold (or Ag) coating the probe then repetitively pressing the probe tip in a controlled fashion onto a flat smooth surface to push the malleable gold (Ag) off the top surface of the probe but still keeping the gold (Ag) inside the hole. Finally one could use the FIB to selectively deposit a metal (e.g. tungsten) just in the hole region in a non-metalized probe tip to create an annular region. With this configuration laser radiation sent down the fiber would be absorbed by the small metalized hole leading to rapid and local beating of just the hole region to provide a sub-micron sized nanoheater source.

Figure 8A:
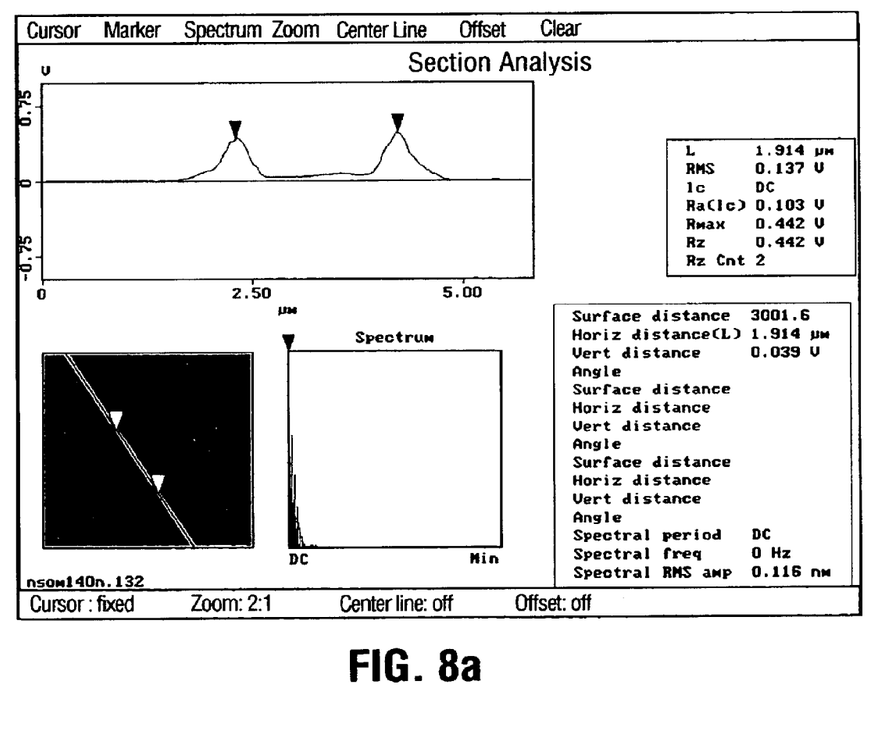
FIG. 8a is an NSOM beam scan at the exit surface of a non-metalized hollow tipped fiber probe showing the annular light distribution.
Figure 8B:
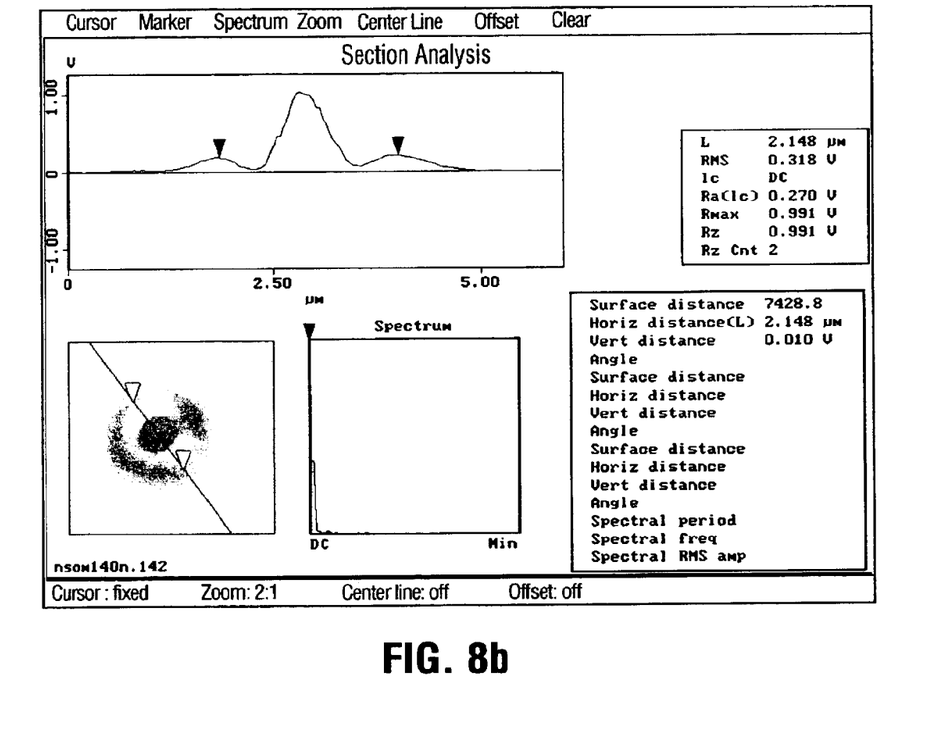
FIG. 8b is an NSOM beam scan at a height of 2 μm above the tip surface showing the filling in of the center of the annulus.

The inventors have demonstrated experimentally using a non-metalized probe in air that the annular beam only extends for about 1 $\mu$m away from the tip and then tends to fill in so that for distances greater than 1 $\mu$m the light distribution approaches a Gaussian distribution as indicated in FIGS. 8a and 8b. It follows that in a fluid the annular light distribution can confine a particle in 2-D within the annulus. At distances >1 $\mu$m from the tip the light distribution attempts to push a particle away from the probe tip. However for a metalized probe with an annular silica waveguide opening the presence of localized surface charging of the sharp tapered metal/silica tip provides an electrostatic restoring force (due to the so-called lightning rod effect) to attract a particle towards the tip surface. It is possible to strike a balance between the two forces to trap a particle in 3-D (e.g a. 2 $\mu$m glass bead) approximately 1 $\mu$m away from the tip. The electrostatic force is enhanced by providing a good electrical conducting path from the probe tip back to a point where the metalized fiber probe is electrically grounded. Usually 10 mW of cw laser radiation (e.g. at $\lambda$=1.3 $\mu$m) coupled into the fiber probe was sufficient to produce optical trapping. Once the particles are trapped they can be transported at high speeds (hundreds of microns per second) to a desired location e.g near the fluid surface and released by shutting off the trapping beam.

It is also possible to combine two lasers: a pulsed laser beam sent down the same probe to biopsy or inject biological material or a drug sample into a cell which is trapped by the cw laser beam as discussed above.

The probes and the laser based extraction injection technique described represent a new and possibly disruptive technology for attoliter biopsy, injection and analysis of biological materials. The technology may also be useful in the field of genetics as a means of transporting extremely small volumes of genetic material such as DNA across cell walls for injection into the nucleus. The probes may also be useful to trap, move and release sub-micron particles for future nanostructuring applications.

The fact that the chemical etching of the fibers can be done in a batch process makes commercialization feasible. Arrays of these fiber probes can be made to sample arrays of specimens trapped, for example, in fixed arrays of holes. The concept of using pulsed laser radiation sent down an optical waveguide terminated in a sub-micron hole to extract or inject attoliter volumes of chemical or biological material can also be applied to biochip sensing applications.

As will be recognized by one skilled in the art, many other variants are possible without departing from the scope of the invention.

We claim:

1. A probe for manipulating small quantities of material, comprising:
    an optical fiber probe having a tip with a hole fabricated therein, said hole being sufficiently small and sufficiently deep that upon immersion of said tip in said material a virtual seal forms to inhibit penetration of said material into said hole; and
    said optical fiber probe providing a waveguide to direct laser radiation to said hole to disrupt said virtual seal and thereby promote entry of said material into said hole.

2. A probe as claimed in claim 1, wherein said tip is sharp to facilitate penetration of said probe into a medium containing said material.

3. A probe as claimed in claim 2, wherein the optical fiber has a portion of reduced diameter adjacent to said sharp tip.

4. A probe as claimed in claim 1, wherein said hole has an aspect ratio of at least 1:1.

5. A probe as claimed in claim 4, wherein said hole has a diameter of 10–200 nm.

6. A probe as claimed in claim 1, wherein said optical fiber has a high $GeO_2$ doped core.

7. A probe as claimed in claim 6, wherein said optical fiber has an $F_2$ doped cladding.

8. A probe has claimed in claim 1, wherein said optical fiber has an index of refraction which is approximately parabolic in shape across said core.

9. A probe as claimed in claim 8, wherein said index of refraction has a narrow central dip in said core that drops approximately to the level of the cladding.

10. A probe as claimed in claim 1, wherein said sharp tip is in the form of a conical structure and said hole is provided on the apex of said conical structure.

11. A probe as claimed in claim 1, wherein the waveguide region surrounding said hole is annular and has a width close to $\lambda/2n$, where n is the refractive index of the waveguide medium surrounding the hole and $\lambda$ is the wavelength of the laser radiation.

12. A method of manipulating a microscopic quantity of material, comprising:
    providing an optical fiber probe having a tip with a hole fabricated therein, said hole being sufficiently small and sufficiently deep that upon immersion of said tip in said material a virtual seal forms to inhibit penetration of said material into said hole;
    immersing said tip in said material; and
    sending laser radiation through said optical fiber probe to disrupt said virtual seal and thereby promote entry of said material into said hole.

13. A method as claimed in claim 12, wherein said tip is sharp to facilitate penetration of said probe into a medium containing said material.

14. A method as claimed in claim 13, wherein said laser radiation is pulsed.

15. A method as claimed in claim 13, wherein said sharp tip has a conical structure.

16. A method as claimed in claim 12, wherein said optical fiber probe forms part of an array of such probes.

17. A method as claimed in claim 16, wherein said array of probes are integrally formed within a common substrate.

18. A method as claimed in claim 17 wherein said array of probes are interfaced with a biochip.

19. A method as claimed in claim 12, wherein said hole has an aspect ratio of at least 1:1.

20. A method as claimed in claim 19, wherein said hole has a diameter of less than 200 nm.

21. A method as claimed in claim 12, wherein material in said hole is subsequently controllably ejected with the aid of a pulsed laser beam.

22. A method as claimed in claim 21, wherein said ejected material is ejected into a living cell.

23. A method as claimed in claim 12, wherein said hole has a diameter of between 10–200 nm.

24. A method as claimed in claim 12, wherein a pulsed laser beam is applied to trap the said material perform a biopsy.

25. A method as claimed in claim 12 wherein said probe is used to promote the entry of a bead containing a drug or a sensor into the hole for ejection into a biological material.

26. A method as claimed in claim 12, wherein material trapped in the hole is injected into a mass spectrometer for constituent analysis.

27. A method of inserting a small quantity of material into a cell, comprising:

immersing in said material an optical fiber probe having a tip with a hole fabricated therein, said hole being sufficiently small that upon immersion of said tip in said material a virtual seal forms to inhibit penetration of said material into said hole;

sending laser pulse radiation said optical fiber probe to disrupt said virtual seal and thereby promote entry of said material into said hole;

inserting said optical fiber probe into said cell; and ejecting said material from said probe into said cell.

28. A method as claimed in claim 27, wherein a pulsed laser beam is applied to said material trapped in said hole to eject said material therefrom.

* * * * *